United States Patent
Cassiday et al.

(10) Patent No.: US 10,240,704 B2
(45) Date of Patent: Mar. 26, 2019

(54) MOLDED FLUID TRANSFER ASSEMBLIES HAVING INCREASED WORKING PRESSURES AND BURST PRESSURES

(71) Applicant: SAINT-GOBAIN PERFORMANCE PLASTICS CORPORATION, Solon, OH (US)

(72) Inventors: Bryan L. Cassiday, Beaverton, MI (US); Mitchell L. Snyder, Hope, MI (US); David Damzyn, Gladwin, MI (US); Thomas R. Nixon, Au Gres, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 427 days.

(21) Appl. No.: 14/986,250

(22) Filed: Dec. 31, 2015

(65) Prior Publication Data
US 2016/0195208 A1 Jul. 7, 2016

Related U.S. Application Data

(60) Provisional application No. 62/098,976, filed on Dec. 31, 2014.

(51) Int. Cl.
*F16L 41/02* (2006.01)
*F16L 31/02* (2006.01)
(Continued)

(52) U.S. Cl.
CPC ............ *F16L 41/02* (2013.01); *A61M 39/10* (2013.01); *F16L 31/02* (2013.01); *F16L 41/021* (2013.01);
(Continued)

(58) Field of Classification Search
CPC ......... F16L 41/02; F16L 41/03; F16L 41/023; F16L 41/021; F16L 43/008;
(Continued)

(56) References Cited

U.S. PATENT DOCUMENTS 4,997,213 A * 3/1991 Traner .................... F16L 31/02
285/131.1 X
5,411,300 A * 5/1995 Mitsui .................. 285/133.11 X
(Continued)

FOREIGN PATENT DOCUMENTS

| CN | 102597592 A | 7/2012 |
| KR | 1020030087435 A | 11/2003 |
| KR | 1020100120449 A | 11/2010 |

OTHER PUBLICATIONS

International Serach Report issued in PCT Application No. PCT/US2015/068305 dated Apr. 8, 2016, 1 page.

*Primary Examiner* — Greg Binda
*Assistant Examiner* — Zachary T Dragicevich
(74) *Attorney, Agent, or Firm* — Abel Law Group, LLP; Chi Suk Kim

(57) ABSTRACT

Embodiments of the present disclosure are directed to a fluid connection including a plurality of flexible polymeric tubes; an integral fluid connector coupled to and in fluid communication with each of the plurality of tubes; and a shell disposed over and encapsulating the fluid connector. The fluid connection surprisingly exhibiting significant increases in the working pressure, particularly in biopharmaceutical fluid transfer systems.

17 Claims, 6 Drawing Sheets

(51) Int. Cl.
*F16L 47/32* (2006.01)
*A61M 39/10* (2006.01)
*F16L 41/03* (2006.01)
*F16L 43/00* (2006.01)
*A61M 39/16* (2006.01)
*A61M 39/12* (2006.01)

(52) U.S. Cl.
CPC ............ *F16L 41/023* (2013.01); *F16L 41/03* (2013.01); *F16L 43/008* (2013.01); *F16L 47/32* (2013.01); *A61M 39/12* (2013.01); *A61M 39/16* (2013.01); *A61M 2207/00* (2013.01); *F16L 2201/44* (2013.01); *Y10T 29/49435* (2015.01)

(58) Field of Classification Search
CPC ....... F16L 2201/44; F16L 47/32; F16L 31/02; A61M 39/10; A61M 39/12; A61M 39/16; A61M 2207/00; Y10T 29/49435
USPC ............ 285/285.1, 294.1, 423, 130.1, 131.1, 285/132.1, 133.11
See application file for complete search history.

(56) References Cited

U.S. PATENT DOCUMENTS

| | | | |
|---|---|---|---|
| 5,447,341 A * | 9/1995 | Hartel | F16L 31/02 285/423 X |
| 6,135,508 A * | 10/2000 | Genoni | 285/285.1 X |
| 7,407,612 B2 | 8/2008 | Warburton-Pitt et al. | |
| 8,424,923 B2 | 4/2013 | Inman, Jr. et al. | |
| 2002/0041096 A1 | 4/2002 | Krause et al. | |
| 2005/0104370 A1* | 5/2005 | Kim | 285/133.11 |
| 2008/0267699 A1 | 10/2008 | Warburton-Pitt et al. | |
| 2009/0243284 A1 | 10/2009 | Klingel, Jr. et al. | |
| 2012/0223517 A1* | 9/2012 | Morrissey | A61M 39/12 |
| 2014/0091569 A1* | 4/2014 | Spohn | A61M 39/12 285/285.1 X |
| 2014/0312617 A1 | 10/2014 | Okabe et al. | |

* cited by examiner

MOLDED FLUID TRANSFER ASSEMBLIES HAVING INCREASED WORKING PRESSURES AND BURST PRESSURES

CROSS-REFERENCE TO RELATED APPLICATION(S)

This application claims priority under 35 U.S.C. § 119(e) to U.S. Patent Application No. 62/098,976 entitled "MOLDED FLUID TRANSFER ASSEMBLIES HAVING INCREASED WORKING PRESSURES AND BURST PRESSURES," by Bryan L. Cassiday et al., filed Dec. 31, 2014, which is assigned to the current assignee hereof and incorporated herein by reference in its entirety.

FIELD OF THE DISCLOSURE

The present disclosure relates to fluid transfer assemblies, and more particularly to, fluid transfer assemblies including a fluid connector and flexible polymeric tubing for biopharmaceutical production.

RELATED ART

Fluid transfer assemblies are used in a variety of applications within fluid processing and management. Particularly, in the context of biopharmaceutical production, the transfer of sensitive fluid is paramount.

Further, in particular fluid transfer systems, specialty tubing materials and connector materials must be used due to the sensitive nature of the fluid and the required. However, a common problem in the industry is the ability to adequately seal the connections between the tubing and connector while being able to sterilize the inner cavities of the tubing and connector. Currently, the working pressure is limited in such assemblies by the strength of the coupling between the tubing.

However, the industry continues to demand higher and higher working pressures to improve the efficiency of production and enable more desirable fluid transfer characteristics.

Accordingly, a need exists to develop better fluid connections methods between tubing. In this vein, the current inventors have been able to surprisingly and significantly increase the working pressure of such fluid connections to the point in some instances that the fluid connection is no longer the point of failure and the tubing itself or testing machine fail before the fluid connection.

BRIEF DESCRIPTION OF THE DRAWINGS

Embodiments are illustrated by way of example and are not limited in the accompanying figures.

Figure 1:
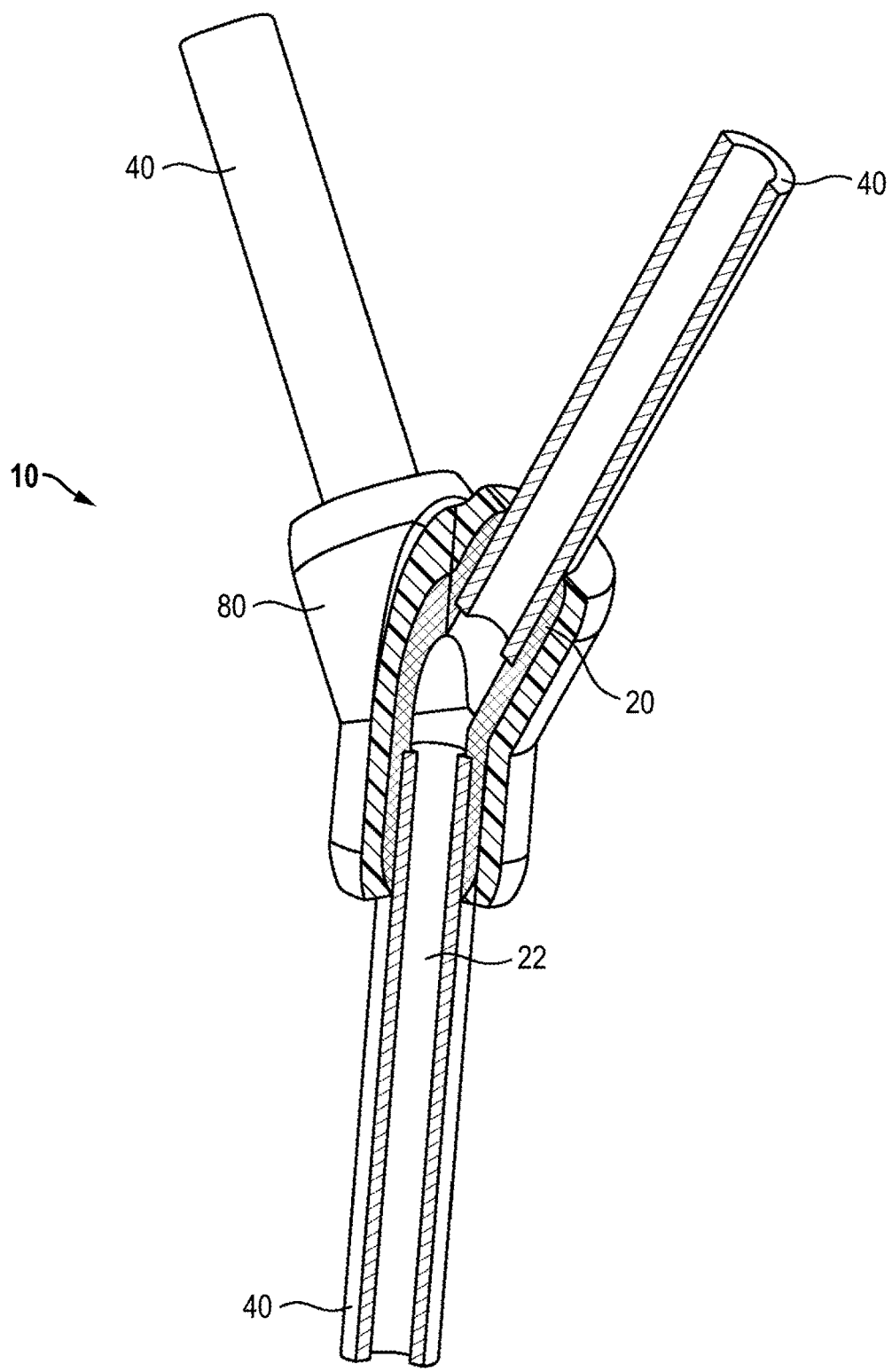
FIG. 1 includes an illustration of a perspective partial cutaway view of a fluid connection in the form of a wye according to one embodiment.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the fluid transfer arts.

The present disclosure is generally directed to fluid connections, and particularly to biopharmaceutical fluid connections including a biopharmaceutical tubing and an integral fluid connector in fluid communication with the tubing. Further, the fluid connection can include a shell encapsulating the fluid connector. Such fluid connections can exhibit significantly higher working pressures than were previously achievable. The concepts are better understood in view of the embodiments described below that illustrate and do not limit the scope of the present invention Referring now to FIGS. 1-4, certain embodiments of a fluid transfer assembly are depicted in which the fluid transfer assembly includes a fluid connection 10 including a plurality of tubes 40 integrally coupled together via a fluid connector 20. The fluid connector 20 has an inner surface 22 that is fluid facing. A shell 80 is disposed about and encapsulating the fluid connector 20 such that the fluid connector 20 is generally not exposed to the outside environment, and the shell 80 is non-fluid facing.

In certain embodiments the tubing 40 can be described as biopharmaceutical tubing. As used herein, biopharmaceutical tubing refers to tubing adapted for use in the biopharmaceutical industry. For example, biopharmaceutical tubing traditionally is autoclavable, or sterilizable, provides a chemical and physical barrier to the fluid being transferred, and is generally inert to the fluid being transferred.

In particular embodiments, the tubes 40 can be flexible tubes. For example, the tubes 40 can contain modulus of elasticity and elongation characteristics that create a substantially flexible tube.

In particular embodiments, the tubes 40 can be flexible polymeric tubes. For example, the tubing can include silicone tubes; thermoplastic tubes, such as a thermoplastic elastomer (TPE) tube, a thermoplastic vulcanizate (TPV) tube, a thermoplastic polyurethane (TPU) tube, a polyamide tube, a styrenic containing tube, or a polyolefin or polyolefin blend tube; a polyethylene tube; a flexible polyvinyl chloride (fPVC) tube, or combinations thereof. In certain embodiments, the fPVC can have a Young's modulus of at least 1 GPa, In very particular embodiments, the tubing can be a silicone tube. In even further particular embodiments, the silicone can be a silicone rubber. The silicone may be formed, for example, using a non-polar silicone polymer. In an example, the silicone polymer may include polyalkylsiloxanes, such as silicone polymers formed of a precursor, such as dimethylsiloxane, diethylsiloxane, dipropylsiloxane, methylethylsiloxane, methylpropylsiloxane, or combinations thereof. In a particular embodiment, the polyalkylsiloxane includes a polydialkylsiloxane, such as polydimethylsiloxane (PDMS). In general, the silicone polymer can be non-polar and essentially free of halide functional groups, such as chlorine and fluorine, and of phenyl functional groups. Alternatively, the silicone polymer may include halide functional groups or phenyl functional groups. For example, the silicone polymer may include fluorosilicone or phenylsilicone.

In an embodiment, the silicone polymer can be a platinum catalyzed silicone formulation. Alternatively, the silicone polymer may be a peroxide catalyzed silicone formulation. In a further embodiment, the silicone polymer can be a platinum and peroxide catalyzed silicone formulation. The silicone polymer may be a liquid silicone rubber (LSR) or a high consistency gum rubber (HCR). In a particular embodiment, the silicone polymer can be a platinum catalyzed LSR. In a further embodiment, the silicone polymer can be an LSR formed from a two part reactive system. Particular embodiments of LSR include Wacker 3003 by Wacker Silicone of Adrian, Mich. and Rhodia 4360 by Rhodia Silicones of Ventura, Calif. In another example, the silicone polymer is an HCR, such as GE 94506 HCR available from GE Plastics. In a particular embodiment, the silicone polymer is a peroxide catalyzed HCR.

In very particular embodiment, the tubing 40 can be a reinforced tubing. For example, reinforcement can be combined with the polymer matrix during formation of the tubing and provide the tubing with desirable characteristics such as improved strength and pressure rating. In certain embodiments, the reinforcement material can include polyester, adhesion modified polyester, polyamide, polyaramid, stainless steel, or combination thereof. In an exemplary embodiment, such as when the reinforcement material is polyester, the polyester can be braided wherein strands of polyester yarn are intertwined. In a further exemplary embodiment, such as when the reinforcement material is stainless steel, the stainless steel can be helical wrapped stainless steel wire. In still further embodiments, the reinforcement material can include a combination of braided polyester and helical wrapped stainless steel wire. In very particular embodiments, the tubing 40 can be a reinforced silicone tubing.

In particular embodiments, such as illustrated in FIGS. 1-4, the fluid connection 10 can include more than one tube 40. For example, depending on the type of fluid transfer and the type of fluid connector, the fluid connection 10 can include a plurality of tubes 40, such as in a range of from 1 to 10 tubes coupled to the same fluid connector. In such embodiments containing multiple tubes, each of the plurality of tubes can be the same, or in other embodiments can be different. It is to be understood that the particular selection of tubing type may depend on, for example, the rate of fluid transfer desired, the pressure rating desired, the type of fluid being transferred, or other factors. In very particular embodiments, the fluid connection 10 can include 2 tubes, 3 tubes, 4 tubes, or more than 4 tubes such as 5 tubes, 6 tubes, 7 tubes, 8 tubes, 9 tubes, or even 10 tubes. In other embodiments, the fluid connection 10 can include more than 10 tubes.

The fluid connection described herein can be employed with a variety of different tube sizes. For example, in particular embodiments, the tubing 40 can have an inner diameter in a range of from about 0.125 inches to about 2.0 inches, or even larger.

Furthermore, in certain embodiments, the tubing 40 can have an outer diameter in a range of from about 0.25 inches to about 2.5 inches, or even larger.

Moreover, tube tubing 40 can have a particular ratio of the outer diameter to the inner diameter. For example, in particular embodiments, a ratio of the outer diameter of the tubing to the inner diameter of the tubing can be in a range of from about 1.1:1 to about 5:1.

In embodiments in which the fluid connection 10 contains more than one distinct tube, the plurality of tubes can have generally the same size, or they can be different. In very particular embodiments, at least one of the plurality of tubes can have a different size than another one of the plurality of tubes.

Figure 2:
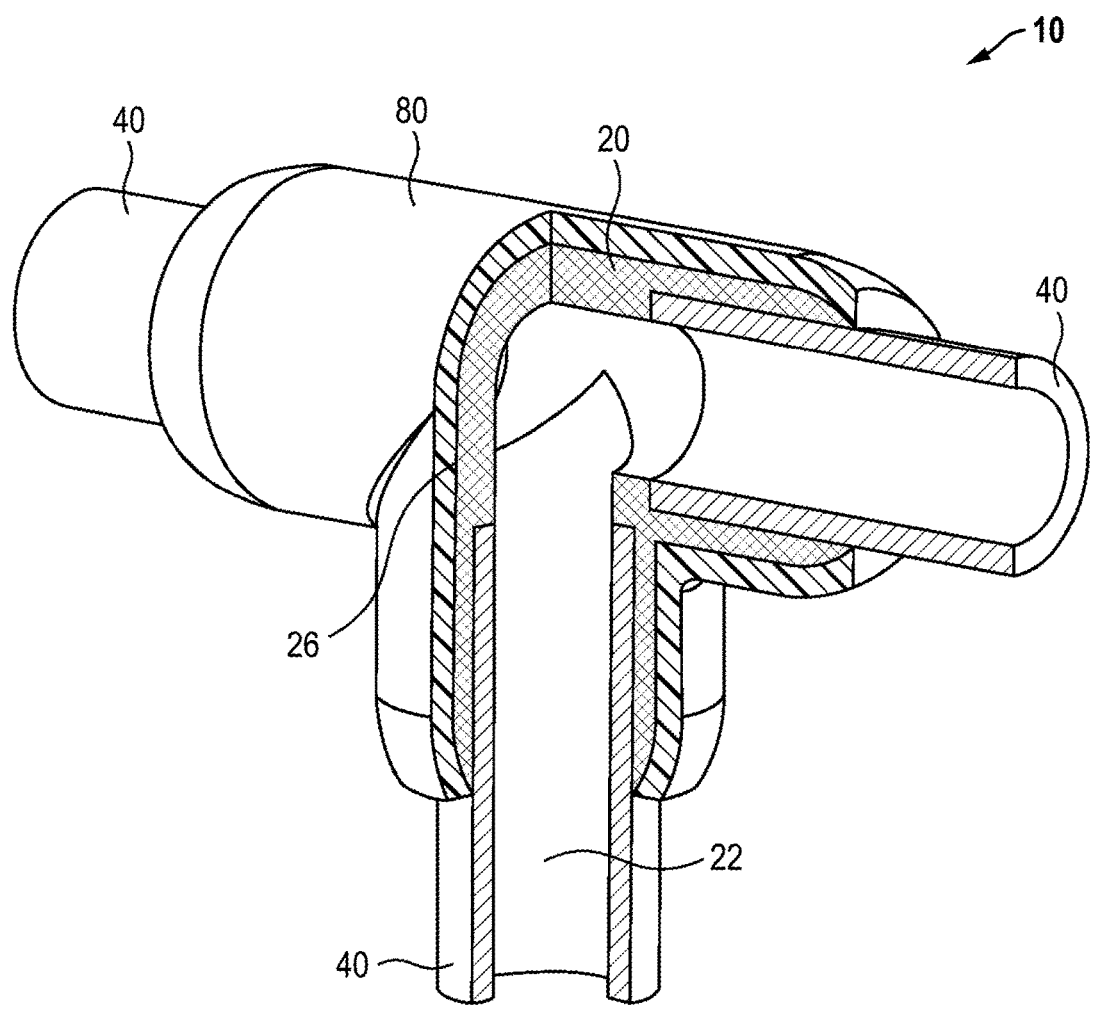
FIG. 2 includes an illustration of a perspective partial cutaway view of a fluid connection in the form of a tee according to one embodiment.
Figure 3:
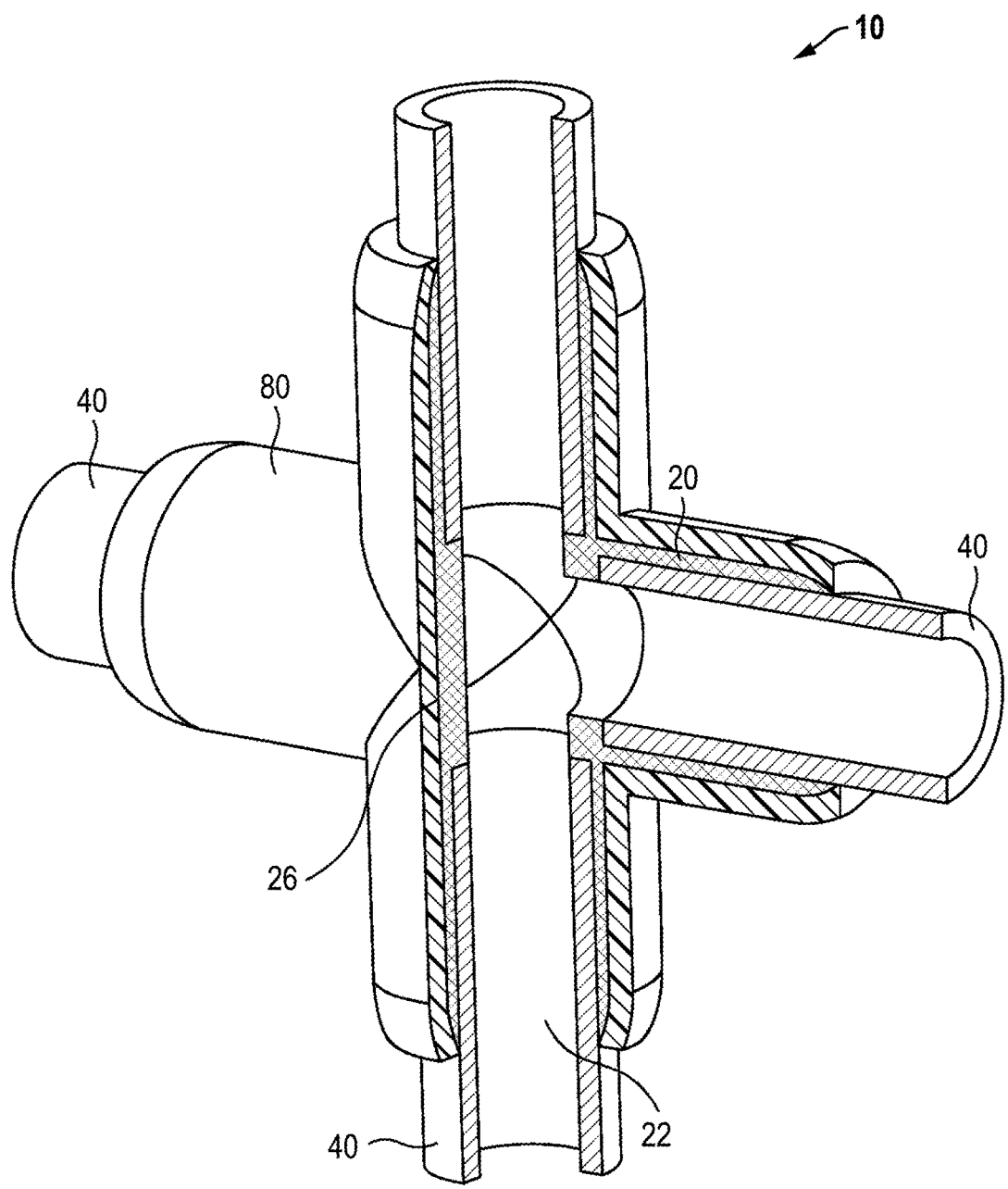
FIG. 3 includes an illustration of a perspective partial cutaway view of a fluid connection in the form of a cross according to one embodiment.
Figure 4:
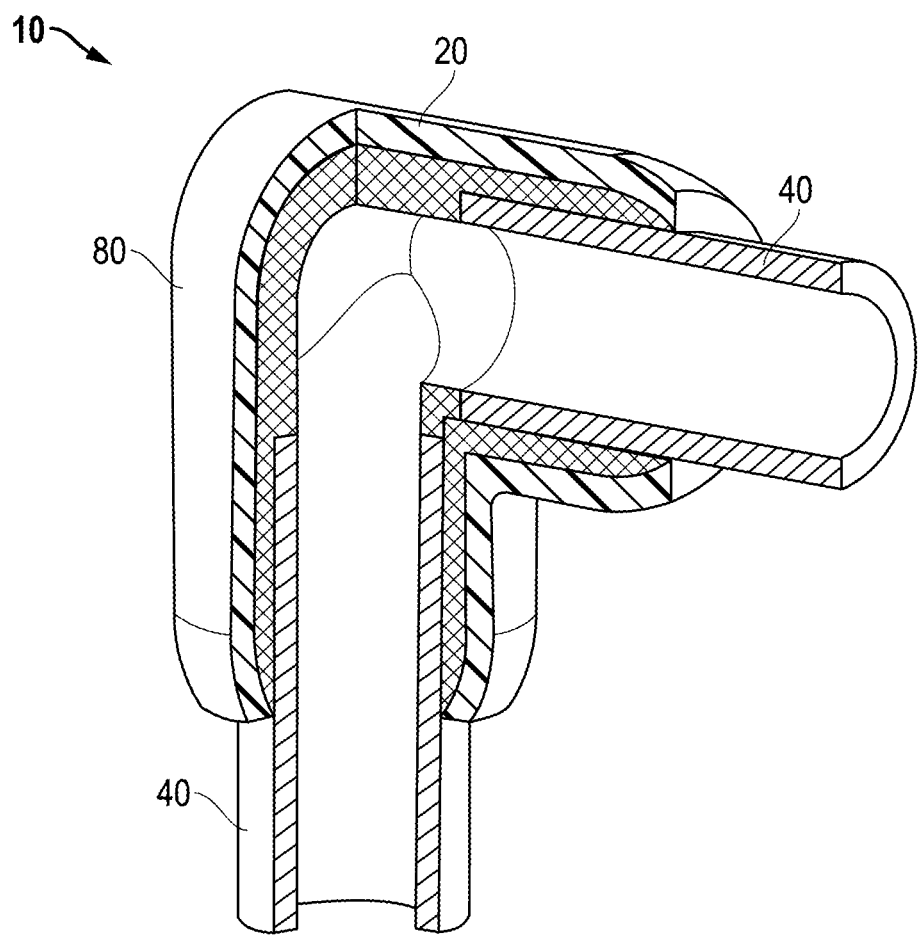
FIG. 4 includes an illustration of a perspective partial cutaway view of a fluid connection in the form of an elbow according to one embodiment.
Figure 5:
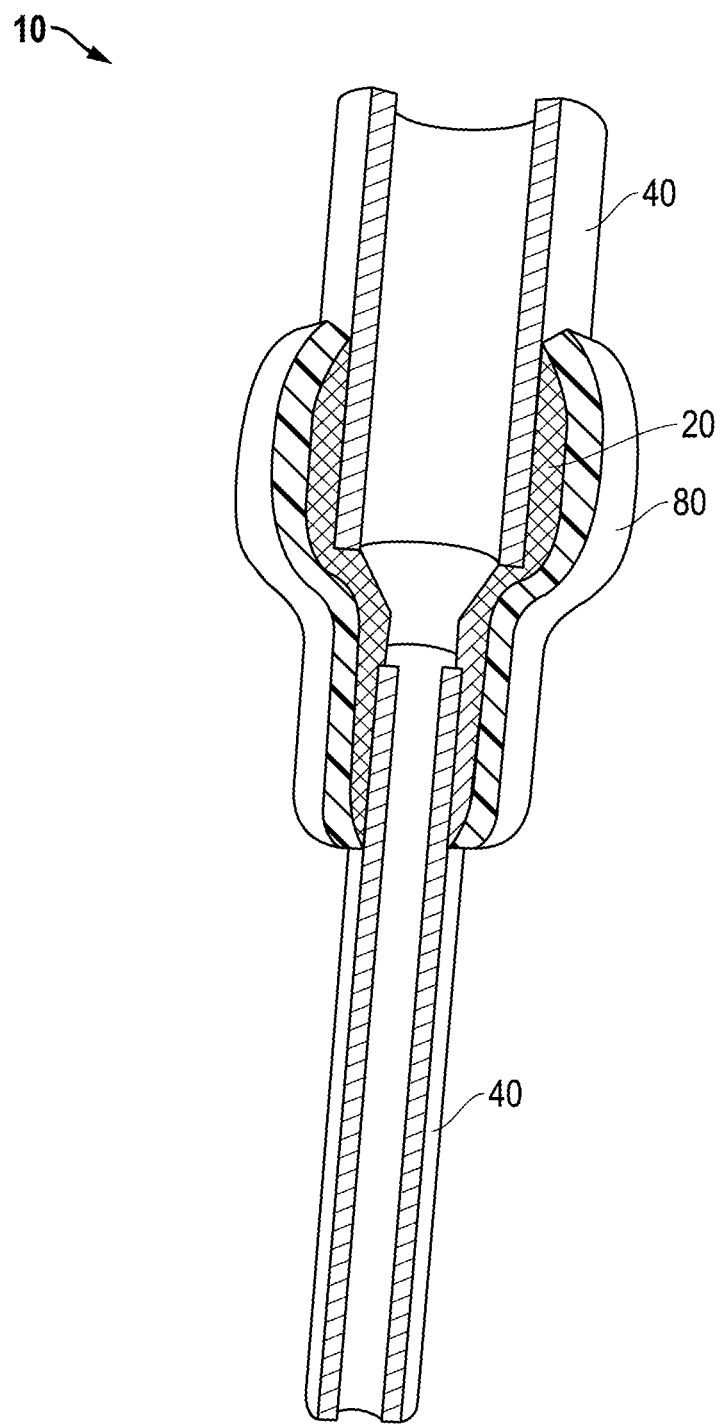
FIG. 5 includes and illustration of a perspective partial cutaway view of a fluid connection in the form of an reducing coupling according to one embodiment.

As described above, and referring again to FIG. 1, the fluid connection 10 can include a fluid connector 20. The fluid connector 20 can take on a generally recognizable form of a tee as illustrated in FIG. 2, a wye as illustrated in FIG. 1, a cross joint as illustrated in FIG. 3, an elbow joint as illustrated in FIG. 4, a straight connector, or any other shape that allows a desired fluid transfer. In particular embodiments, the fluid connector can be a reducing coupling connecting tubing of a relatively larger inner diameter to a tubing of a relatively smaller inner diameter, as illustrated in FIG. 5.

In fact, a particular advantage of certain embodiments of the present disclosure is the diversity of possible shapes and sizes of the fluid connector and tubing and the improvements in working pressure across the range of different fluid connector shapes. For example, and as will be discussed in more detail below, the fluid connector can be directly formed and molded onto the tubing as described in, for example, U.S. Pat. No. 7,407,612, which is incorporated herein by reference for all useful purposes. Since the fluid connector does not need to be preformed, a greater flexibility in the shapes, sizes and number of connected tubes can be created.

The fluid connector 20 can be composed of a variety of different materials. For example, in certain embodiments, the fluid connector 20 can include a polymeric material.

In particular embodiments, the fluid connecter 20 can be made of a thermoset polymer such as a silicone material. The silicone can be any of the silicone materials described above, such as LSR or HCR. In particular embodiments, the silicone material can be injection moldable. For example, the silicone material can have a particular viscosity that enables injection molding.

In other embodiments, the fluid connecter can be made of a thermoplastic material such as such a thermoplastic elastomer such as TPV, TPU, TPE, fPVC, or combinations thereof.

In particular embodiments, the fluid connector can be made of a material which can withstand the temperatures and pressures of an autoclave after formation, and thus be autoclavable. For example, silicone is widely recognized as a material which can withstand autoclave after curing and treatment.

In certain embodiments, the fluid connector 20 can be made of the same general class of base polymers as the tubing 40. For example, the tubing 40 can be silicone tubing, and the fluid connector 20 may also be made from a silicone material. In other embodiments, they can be different. In particular embodiments, the tubing 40 can be reinforced silicone tubing, and the connector 20 may also be made from a silicone material. Still further, in such embodiments, the fluid connector 20 may be made from an unreinforced silicone material.

The fluid connector 20 can be fluid facing as illustrated in FIGS. 1-5. For example, the fluid connector 20 can form part of the inner cavity 28 of the fluid connection 10 such that it may contact the fluid being transferred. Accordingly, in particular embodiments, the connector 20 can be adapted to be inert to the fluid being transferred, made of a generally inert material, or otherwise considered generally inert. As described above, silicone is one such material that is considered generally inert in this context.

The fluid connector 20 can be integral with or integrally coupled to the plurality of tubes 40. For example, as described elsewhere herein, the fluid connector 20 can be formed directly onto and bonded with the plurality of tubes. Accordingly, in such embodiments, the fluid connector 20 can be integral with or integrally coupled to the plurality of tubes 40.

Figure 6:
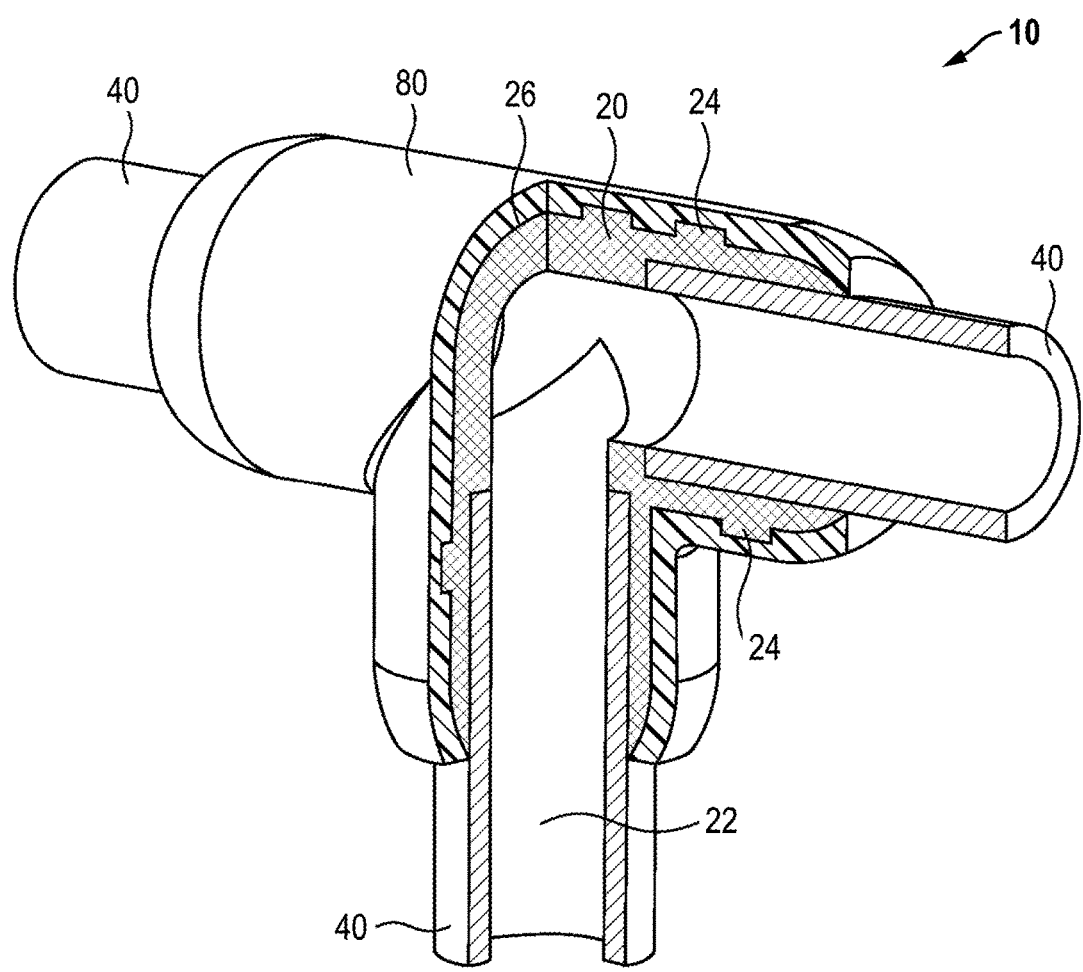
FIG. 6 includes an illustration of a perspective partial cutaway view of a fluid connection with a fluid connector having a plurality of outer surface features according to one embodiment.

Referring to FIG. 6, in certain embodiments, the fluid connector 20 can include one or more outer surface features 24. For example, the one or more outer surface features 24 can include protrusions, depressions, grooves, channels, or the like, or any other feature that can improve the coupling between the fluid connector and the shell. The one or more outer surface features of the fluid connector can make intimate contact with the shell. For example, and as discussed in more detail below, the shell can be directly overmolded over the fluid connector, and since the shell material is flowable during initial contact with the fluid connector, an intimate contact with the shell about the one or more surface features is possible.

In particular embodiments, the one or more outer surface features 24 of the fluid connector 20 can be monolithic with body of the fluid connector 20. For example, as discussed in more detail below, the fluid connector can be formed by overmolding onto the tube ends. Accordingly, a mold used to form the fluid connector can include a profile that is adapted to form the one or more outer surface features simultaneously with forming the fluid connector. Accordingly, the one or more surface features can be monolithic with the body of the fluid connector and be formed of the same material as the fluid connector.

In certain embodiments, the outer surface 26 of the fluid connector can include a surface treatment. A surface treatment can include an increased surface roughness as compared to when the fluid connector is initially formed. In further embodiments, a surface treatment can include a chemical treatment. The surface treatment can be adapted to improve the coupling between the fluid connector and the shell.

Referring again to FIGS. 1-4, the fluid connection 10 further includes a shell 80 encapsulating the fluid connector 20.

The shell 80 can be made from a desirable material. For example, the shell 80 can be made from a material that is capable of, or adapted to, substantially prevent the fluid connector from expanding due to increased fluid pressure within the fluid connection.

Accordingly, in particular embodiments, the shell 80 can have a higher stiffness, hardness, and/or rigidity than the fluid connector 20.

In other embodiments, the shell 80 can have a lower stiffness, hardness, and/or rigidity that the fluid connector 20.

In particular embodiments, the shell 80 can be made from a polymer material. For example, the shell can be made from a thermoplastic material, such as a thermoplastic elastomer. Specific examples of suitable polymer materials can include polypropylene.

In particular embodiments the shell 80 can be a monolithic piece, also referred to as a single piece. For example, and as discussed in more detail herein, the shell can be formed by overmolding the joined tubing and fluid connector. Such overmolding operation can result in a unified monolithic shell. Further, the shell material can be described as an injection moldable material.

As further illustrated in FIGS. 1-4, the shell 80 can be unexposed to the inner cavity 42 of the tubing 40 and the inner cavity 28 of the fluid connector 20 such that the shell 80 is non-fluid facing. For example, and as discussed in more detail below, the fluid connection 10 can be formed by forming the fluid connector 20 about the tubing 40, and following, forming the shell 80 over the tubing 40 and particularly, encapsulating the fluid connector 20. Accordingly, there is always another layer of material other than the shell 80, such as the fluid connector 20 or tubes 40, forming a fluid facing surface of the inner cavities 42, 28 of the fluid connection 10 and as such the shell 80 is not fluid facing.

In particular embodiments, the shell 80 can be made of a material which can withstand the temperatures and pressures of an autoclave after formation, and thus be autoclavable. For example, polypropylene is generally recognized as a material which is autoclavable.

In other embodiments, the shell 80 can be made of a material which does not need to withstand the temperatures and pressures of an autoclave after formation, and thus not be autoclavable. For example, and as will be discussed in more detail below, particular embodiments of the present disclosure include sterilizing the fluid connection without the presence of the shell, and then after, forming the shell 80 over and encapsulating the fluid connection. In such a way, the inner cavities can be sterilized, and the shell can be formed of a material which does not need to withstand autoclave, thus broadening the range of materials which can form the shell. One reason such sterilization procedures are possible is because of the fluid connector's integral coupling to the tubes, such as by overmolding, to achieve a fluid tight connection with a pressure rating of at least about 15 psi such that the fluid connection can be autoclaved without the shell. Accordingly, the inside cavities of the tube and fluid connector can remain antiseptic during formation of the shell.

The shell 80 can include a first end 89, disposed furthest from the center of the fluid connector 20. In particular embodiments, the first end 89 can be tapered toward the tube 40. In particular embodiments, the first end 89 can be tapered toward the tube 40 and contact the tube 40 such that the fluid connector is not exposed past the first end of the shell. In other embodiments, the fluid connector 20 can extend past the first end 89 of the shell and be exposed to the outside environment.

In certain embodiments, the fluid connection 10 can be essentially free of an adhesive. For example, as discussed in more detail below, the fluid connector 20 can be directly molded onto the tubes 40, and the shell 80 can be directly molded over the fluid connector 20 thereby eliminating the need for an adhesive. In general, biopharmaceutical applications prefer the absence of adhesives to decrease the risk of contamination of the fluid. For example, typical adhesives can be aggressive, reactive materials that could leach through materials of the fluid connection and potentially interact with and contaminate the fluid being transferred. Further, employment of adhesives were typically necessary when forming fluid connections to obtain an adequate seal. Accordingly, a particular advantage of certain embodiments of the present disclosure is the ability to form a fluid connection that is essentially free of an adhesive, particularly in combination with other features described herein, such as the increased working pressure.

In other embodiments, an adhesive layer can be disposed between the fluid connector and the shell to improve adhesion of the shell to the fluid connector. When employed, such an adhesive should, in some embodiments, be capable of withstanding an autoclave.

As discussed herein, particular embodiments are directed to a biopharmaceutical fluid connection such that the fluid facing materials are generally inert to the fluid being transferred, and the fluid connection can be sterilized in, for example, an autoclave. Further, the materials used for the tubing, fluid connector and/or shell can be essentially free of peroxide by-products, chlorophenyls, or PCBs, organic plasticizers, phthalates, or latex additives. In more particular embodiments, the tubing and fluid connector can be essentially free of peroxide by-products, chlorophenyls, or PCBs, organic plasticizers, phthalates, or latex additives.

As described herein, embodiments of the present disclosure can exhibit a substantially improved increase in the working pressure. The working pressure of the fluid transfer assembly is defined as the pressure at which an air leak occurs in any of the components of the fluid connection, such as the tube, the fluid connector, and/or the shell.

Typically the limit of the working pressure in such fluid transfer assemblies has been the coupling between the tubing and the fluid connector or the fluid connector itself. For example, since the fluid connector is a fluid facing material, biopharmaceutical applications demand specialty materials that will not interact with a sensitive fluid. These specialty materials alone can not meet the rigorous demands in biopharmaceutical applications while also capable of withstanding high working pressures. As will be illustrated in more detail in the Examples below, the fluid connections of the present disclosure have been substantially improved to the point that, in some embodiments, the coupling between the fluid connector and the tubing or the fluid connector itself is no longer the weak point, or point of failure in such fluid transfer assembly when testing the working pressure. Moreover, attempts to increase the working pressure of the tubing, by using stronger, higher rated tubing, such as reinforced tubing further complicates the bondability to the fluid connector and thus limits the achievable total working pressure of the fluid connection as a whole. In contrast, the present inventors have discovered that inclusion of a shell as described herein disposed over and encapsulating the fluid connector can significantly increase the working pressure even to the point that the fluid connection is no longer the limiting factor in the working pressure of a fluid transfer assembly. Such a substantial increase in the fluid connection strength and integrity was entirely unexpected. In fact, in certain embodiments, as will be demonstrated by the examples below, the increase in working pressure was so significant, that the testing machine failed before the fluid connection failed. Accordingly, the fluid connection can have a remarkably improved working pressure.

In very particular embodiments, the fluid connection 10 can have a working pressure of at least about 120 psi, at least about 140 psi, at least about 160 psi, at least about 180 psi, at least about 200 psi, at least about 220 psi, at least about 240 psi, at least about 260 psi, at least about 280 psi, at least about 300 psi, at least about 320 psi at least about 330 psi, at least about 360 psi, at least about 380 psi, or even at least about 400 psi, at least about 420 psi, at least about 440 psi, at least about 460 psi, at least about 480 psi, at least about 500 psi, at least about 550 psi, or even at least about 600 psi. In further embodiments, the fluid connection can have a working pressure of no greater than about 2000 psi, no greater than about 1500 psi, or even no greater than 1000 psi. Moreover, the fluid connection can have a working pressure in a range of any of the minimums or maximums provided above, such as in a range of from about 140 psi to about 2000 psi, or even from about 200 psi to about 1500 psi.

The working pressure of the fluid connection according to certain embodiments can be described as a ratio measuring the increase in working pressure of the same fluid connection without the shell. For example, a ratio of the working pressure of the fluid connection to the same fluid connection without the shell can be at least about 1.1:1, at least about 1.2:1, at least about 1.3:1, at least about 1.4:1, at least about 1.5:1, at least about 1.6:1, at least about 1.7:1, at least about 1.8:1, at least about 1.9:1, at least about 2.0:1, at least about 2.5:1, at least about 3.0:1, at least about 3.5:1, at least about 4:1, at least about 4.5:1, or even at least about 5:1. In further embodiments, a ratio of the working pressure of the fluid connection to the same fluid connection without the shell can be no greater than about 1000:1, no greater than bout 500:1, no greater than about 100:1, or even no greater than about 50:1. Moreover, a ratio of the working pressure of the fluid connection to the same fluid connection without the shell can be in a range of any of the minimums or maximums provided above, such as in a range of from about 1.2:1 to about 500:1, or even from about 2.0:1 to about 100:1.

In very particular embodiments, the limit of the working pressure of the fluid connection can be the tubing, and not the coupling between the tubing, i.e. the coupling formed with the fluid connector.

Another aspect of the present disclosure is directed to a fluid transfer assembly comprising one or more fluid connections. It is to be understood that each of the characteristic and embodiments of the fluid connection, fluid connector, tubes, and shell described above are equally applicable to the aspects of the present disclosure directed to fluid transfer assemblies.

In particular embodiments, the fluid transfer assembly can include at least one, such as at least 2, at least 3, or even at least 4 fluid connections. Each of the plurality of fluid connections can be generally the same or they can be different. For example, the fluid transfer assembly can include a three way fluid connection such as a tee, and a four way fluid connection such as a cross.

In particular embodiments, the fluid transfer assembly can be adapted to be disposable or single-use. For example, in the biopharmaceutical industry, there is a continued desire to use disposable or single-use assemblies to increase control and reduce contaminations and costly cleaning and maintenance. Accordingly, the meet the disposable or single use demands of the biopharmaceutical industry, fluid transfer assemblies must be made of relatively low cost materials which has traditionally limited the achievable working pressures of such systems. In contrast, the present inventors have surprisingly discovered a mechanism to increase the working pressure in such disposable or single use systems while using the same types of tubing at a low cost.

Another aspect of the present disclosure is directed to a method of forming a fluid connection. For example, in certain embodiments a method of forming a fluid connection can generally include:
a. providing a plurality of tubes;
b. integrally forming a fluid connector about the plurality of tubes;
c. forming a shell over and encapsulating the fluid connector.

It is to be understood that each of the characteristic and embodiments of the fluid transfer assembly, fluid connector, tubes, and shell described above is equally applicable to the aspect of the present disclosure directed to methods of forming a fluid connection.

In certain embodiments, forming a fluid connector can include overmolding the fluid connector about the one or more tubes.

In certain embodiments, forming a shell over and encapsulating the fluid connector can include overmolding the shell about the fluid connector.

In certain embodiments, the method can further include sterilizing the fluid connection, such as sterilizing the inner cavities of the fluid connection in, for example, an autoclave.

In particular embodiments, sterilizing can occur before formation of the shell. In other embodiments, sterilizing can occur after formation of the shell.

In certain embodiments, the method can further include treating the outer surface of the fluid connector before formation of the shell. For example, in particular embodiments, treating the outer surface of the fluid connector can include increasing the surface roughness, chemical treating, or combinations thereof. The treatment of the outer surface of the fluid connector can be adapted to increase the adhesion strength between the fluid connector and the shell.

In further embodiments, the method can further include forming one or more outer surface features on the fluid connector. For example, the one or more outer surface features can include protrusions, depressions, grooves, channels, or the like, or any other feature that can improve the coupling between the fluid connector and the shell.

In very particular embodiments, forming one or more outer surface features on the fluid connector can occur simultaneously with the formation of the fluid connector. For example, as discussed above, formation of the fluid connector can include overmolding. Accordingly, the mold used when performing overmolding can include a profile that imparts an outer surface feature as described above during the overmolding operation to create the fluid connector. As such, when the shell is formed over and encapsulating the fluid connector, the flowable shell material can make an intimate contact with the outer surface of the fluid connection, including intimately around the surface features, without the need to preform a shell having a complementary profile.

In other embodiments, the outer surface of the fluid connector can be generally smooth. For example, in certain embodiments, the shell essentially completely encapsulates the fluid connector, and the use of outer surface features on the fluid connector may not be needed.

Another aspect of the present disclosure is directed to increasing the working pressure of a fluid connection. In general, certain embodiments of a method of increasing the working pressure of a fluid connection can include:
a. providing a fluid connection comprising a plurality of tubes integrally coupled to a fluid connector; and
b. forming a shell over and encapsulating the fluid connector thereby increasing the working pressure of the fluid connection.

It is to be understood that all of the characteristics and embodiments of the fluid transfer assemblies, fluid connector, methods, tubes, and shell described herein is equally applicable to the embodiments of the present disclosure directed to methods of increasing the working pressure of a fluid connection. For example, the entire range of working pressures and ratios of working pressures described above apply to the methods of increasing the working pressure. As a particular example, the method can include increasing the working pressure of the fluid connection such that a ratio of the working pressure of the fluid connection after formation of the shell the same fluid connection before formation of the shell is at least about 1.2:1, at least about 1.3:1, at least about 1.4:1, at least about 1.5:1, at least about 1.6:1, at least about 1.7:1, at least about 1.8:1, at least about 1.9:1, at least about 2.0:1, at least about 2.5:1, at least about 3.0:1, at least about 3.5:1, at least about 4:1, at least about 4.5:1, or even at least about 5:1 as recited above.

The concepts described herein will be further described in the following examples, which do not limit the scope of the invention described in the claims.

Examples

In the following Example, Samples 1 to 6 were subjected to a burst rating test according to ASTM D380-94(2012). Each Sample tested includes an Example and a Comparative Example. For each of Samples 1 to 6, the Example includes a fluid connection according to an embodiment described herein including a biopharmaceutical tubing, an overmolded fluid connector in fluid communication with the tubing, and a shell encapsulating the fluid connector, whereas the Comparative (Comp.) Example is identical to the Example except that the Comp. Example does not include the shell encapsulating the overmolded fluid connector.

For each Sample, the overmolded connector includes a high durometer silicone material having a Shore A durometer hardness of at least 70 directly formed and molded onto the tubing. For each Example, the shell includes a polypropylene material (P5MK6-080 PPAF available from Flint Hills Resources at Marysville, Mich., USA) directly overmolded over and encapsulating the fluid connector.

The shape of the coupling and the material of the tubing used are described in Table 1. The one or more of the leak tests described above.

The results of the tests are provided below in Table 1. For each sample, the Example comprising the shell exhibits an unexpectedly high increase in burst rating. The particular increase in burst rating for each sample is provided below in Table 1.

TABLE 1

| Sample | Coupling | Tubing | Comp. Example Burst Rating (psi) | Example Burst Rating (psi) | Increase |
|---|---|---|---|---|---|
| 1 | E | A and B | 192 | 252 | 31% |
| 2 | A | A | 125 | 225 | 80% |
| 3 | C | B | 174 | 343 | 97% |
| 4 | B | C | 25 | 96 | 284% |
| 5 | C | C | 25 | 116 | 364% |
| 6 | D | C | 25 | 132 | 428% |

Coupling A refers to a fluid connection having a wye shape as illustrated in FIG. 1.

Coupling B refers to a fluid connection having a tee shape as illustrated in FIG. 2.

Coupling C refers to a fluid connection having a cross shape as illustrated in FIG. 3.

Coupling D refers to a fluid connection having an elbow shape as illustrated in FIG. 4.

Coupling E refers to a reducing fluid connection having the shape illustrated in FIG. 5.

Tubing A refers to a Sani-Tech® STHT®-R platinum-cured braid-reinforced silicone tubing having an inner diameter of about 0.375 inches and an outer diameter of about 0.625 inches (available from Saint-Gobain Performance Plastics Corporation at Northborough, Mass. USA).

Tubing B refers to a Sani-Tech® STHT®-R platinum-cured braid-reinforced silicone tubing having an inner diameter of about 0.5 inches and an outer diameter of about 0.875 inches (available from Saint-Gobain Performance Plastics Corporation at Northborough, Mass. USA).

Tubing C refers to a Sani-Tech® STHT®-R platinum-cured braid-reinforced silicone tubing having an inner diameter of about 1 inch and an outer diameter of about 1.375 inches (available from Saint-Gobain Performance Plastics Corporation at Northborough, Mass. USA).

Tubing D refers to an animal-derived component free (ADCF) C-Flex® thermoplastic elastomer biopharmaceutical tubing having an inner diameter of about 0.0625 inches and an outer diameter of about 0.1875 inches (available from Saint-Gobain Performance Plastics Corporation at Northborough, Mass. USA).

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. A fluid connection comprising:
a. a plurality of flexible polymeric tubes;
b. an integral fluid connector coupled to and in fluid communication with each of the plurality of tubes,
c. a shell disposed over and encapsulating the fluid connector.

Item 2. A fluid connection comprising:
a. a plurality of flexible biopharmaceutical tubes; and
b. an integral fluid connector coupled to and in fluid communication with each of the plurality of tubes;
c. wherein the fluid connection has a working pressure of at least about 120 psi.

Item 3. A fluid connection comprising:
a. a plurality of flexible polymeric tubes comprising an inner cavity;
b. an integral fluid connector coupled to each of the plurality of tubes, the fluid connector having an inner cavity, wherein the inner cavity of the polymeric tubes is in fluid communication with the inner cavity of the fluid connector
c. wherein the inner cavity of the flexible polymeric tubes is aseptic;
d. wherein the inner cavity of the fluid connector is aseptic; and
e. wherein the shell is composed of a material which is non-autoclavable.

Item 4. A fluid connection comprising:
a. a plurality of tubes;
b. a fluid connector, wherein the plurality of tubes are coupled to the fluid connector and form a fluid connection between the plurality of tubes; and
c. a shell disposed over and encapsulating the fluid connector;
d. wherein the coupling of the fluid connector with the plurality of tubes is the first point of failure in the working pressure of the fluid connection before addition of the shell, and wherein after addition of the shell disposed over and encapsulating the fluid connector, the coupling of the fluid connector with the plurality of tubes is not the first point of failure in the working pressure of the fluid transfer assembly.

Item 5. An autoclavable biopharmaceutical fluid connection comprising:
a. a plurality of silicone reinforced tubes;
b. an integral silicone fluid connecter coupled to the plurality of tubes such that there is an essentially seamless transition between the inner cavity of the plurality of tubes and the fluid connector, and wherein the fluid connector is covalently bonded to the tubes; and
c. a polypropylene shell disposed over and encapsulating fluid connector.

Item 6. A fluid transfer assembly comprising one or more of the fluid connections according to any one of the preceding items.

Item 7. A method of forming a fluid connection, the method comprising:
a. providing a plurality of tubes;
b. integrally forming a fluid connector about the plurality of tubes;
c. forming a shell over and encapsulating the fluid connector.

Item 8. A method of increasing the working pressure of a fluid transfer connection, the method comprising:
a. providing a fluid connection comprising a plurality of tubes integrally coupled to a fluid connector;

b. forming a shell over and encapsulating the fluid connector, wherein a ratio of the working pressure of the fluid connection after formation of the shell the same fluid connection before formation of the shell is at least about 1.2:1.

Item 9. The fluid connection, fluid transfer assembly, or method of any one of the preceding items, wherein the fluid connection comprises one or more tubes coupled to the fluid connector.

Item 10. The fluid connection, fluid transfer assembly, or method of any one of the preceding items, wherein the fluid connection comprises 2 tubes, 3 tubes, 4 tubes, 5 tubes, 6 tubes, 7 tubes, 8 tubes, 9 tubes, or even 10 tubes.

Item 11. The fluid connection, fluid transfer assembly, or method of any one of the preceding items, wherein at least one, or even all of the tubes are biopharmaceutical tubes.

Item 12. The fluid connection, fluid transfer assembly, or method of any one of the preceding items, wherein at least one, or even all of the tubes are polymer tubes.

Item 13. The fluid connection, fluid transfer assembly, or method of any one of the preceding items, wherein at least one, or even all of the tubes are thermoplastic tubes.

Item 14. The fluid connection, fluid transfer assembly, or method of any one of the preceding items, wherein at least one, or even all of the tubes are thermoplastic elastomeric tubes.

Item 15. The fluid connection, fluid transfer assembly, or method of any one of the preceding items, wherein at least one, or even all of the tubes are reinforced polymer tubes.

Item 16. The fluid connection, fluid transfer assembly, or method of any one of the preceding items, wherein at least one, or even all of the tubes are reinforced silicone tubes.

Item 17. The fluid connection, fluid transfer assembly, or method of any one of the preceding items, wherein the fluid connector is integral with the tubes.

Item 18. The fluid connection, fluid transfer assembly, or method of any one of the preceding items, wherein the fluid connector is covalently bonded to the tubes.

Item 19. The fluid connection, fluid transfer assembly, or method of any one of the preceding items, wherein the fluid connector has a shape of a tee, wye, elbow, cross joint, or straight connector.

Item 20. The fluid connection, fluid transfer assembly, or method of any one of the preceding items, wherein the fluid connector is overmolded about the tubes.

Item 21. The fluid connection, fluid transfer assembly, or method of any one of the preceding items, wherein the fluid connector is bonded directly the tubes.

Item 22. The fluid connection, fluid transfer assembly, or method of any one of the preceding items, wherein the fluid connector directly contacts the tube.

Item 23. The fluid connection, fluid transfer assembly, or method of any one of the preceding items, wherein the fluid connector has an inner cavity in fluid communication with the inner cavity of the tubes.

Item 24. The fluid connection, fluid transfer assembly, or method of any one of the preceding items, wherein the fluid connector is fluid facing.

Item 25. The fluid connection, fluid transfer assembly, or method of any one of the preceding items, wherein the fluid connector has an inner cavity that is generally inert to a fluid being transferred.

Item 26. The fluid connection, fluid transfer assembly, or method of any one of the preceding items, wherein the inner cavity of the fluid connector has an essentially seamless transition with the tubes.

Item 27. The fluid connection, fluid transfer assembly, or method of any one of the preceding items, wherein the fluid connector has a lower glass transition temperature (Tg) than the tubing, and wherein the shell has a lower glass transition temperature (Tg) than the fluid connector.

Item 28. The fluid connection, fluid transfer assembly, or method of any one of the preceding items, wherein the fluid connector is composed of a material that is compatible with tubing.

Item 29. The fluid connection, fluid transfer assembly, or method of any one of the preceding items, wherein at least one, or even all of the tubes have an outer major surface, and an outer minor surface generally perpendicular the outer major surface, and wherein the fluid connector is disposed adjacent to, or even directly contacting a portion of the outer major surface of the tubes and essentially all of the outer minor surface of the tube.

Item 30. The fluid connection, fluid transfer assembly, or method of any one of the preceding items, wherein the outer surface of fluid connector comprises one or more surface features.

Item 31. The fluid connection, fluid transfer assembly, or method of any one of the preceding items, wherein the outer surface of fluid connector comprises one or more surface features comprising a protrusion, a depression, a groove, a channel, or combinations thereof.

Item 32. The fluid connection, fluid transfer assembly, or method of any one of the preceding items, wherein the outer surface of fluid connector comprises one or more surface features adapted to improve the coupling between the fluid connector and the shell.

Item 33. The fluid connection, fluid transfer assembly, or method of any one of the preceding items, wherein the assembly comprises a shell disposed over and encapsulating the fluid connector.

Item 34. The fluid connection, fluid transfer assembly, or method of any one of the preceding items, wherein the shell comprises polypropylene.

Item 35. The fluid connection, fluid transfer assembly, or method of any one of the preceding items, wherein the shell consists essentially of polypropylene.

Item 36. The fluid connection, fluid transfer assembly, or method of any one of the preceding items, wherein the shell is monolithic.

Item 37. The fluid connection, fluid transfer assembly, or method of any one of the preceding items, wherein the shell is rigid.

Item 38. The fluid connection, fluid transfer assembly, or method of any one of the preceding items, wherein the shell has a hardness greater than the hardness of the fluid connector.

Item 39. The fluid connection, fluid transfer assembly, or method of any one of the preceding items, wherein the shell has a hardness greater than the hardness of the tubing.

Item 40. The fluid connection, fluid transfer assembly, or method of any one of the preceding items, wherein the shell is non-fluid facing.

Item 41. The fluid connection, fluid transfer assembly, or method of any one of the preceding items, wherein the shell is composed of a material that is incompatible with the tubing.

Item 42. The fluid connection, fluid transfer assembly, or method of any one of the preceding items, wherein the shell is composed of a material that is incompatible with the fluid connector.

Item 43. The fluid connection, fluid transfer assembly, or method of any one of the preceding items, wherein the shell is composed of an autoclavable material.

Item 44. The fluid connection, fluid transfer assembly, or method of any one of the preceding items, wherein the shell is not composed of an autoclavable material.

Item 45. The fluid connection, fluid transfer assembly, or method of any one of the preceding items, wherein the fluid connection is autoclavable.

Item 46. The fluid connection, fluid transfer assembly, or method of any one of the preceding items, wherein the fluid connection is adapted to be disposable.

Item 47. The fluid connection, fluid transfer assembly, or method of any one of the preceding items, wherein the fluid connection is adapted to be a single-use fluid connection.

Item 48. The assembly or method of any one of the preceding items, wherein the fluid transfer assembly has a working pressure of at least about 200 psi, at least about 220 psi, at least about 240 psi, at least about 260 psi, at least about 280 psi, at least about 300 psi, at least about 320 psi, or even at least about 340 psi.

Item 49. The assembly or method of any one of the preceding items, wherein the fluid transfer assembly has a working pressure of not greater than about 1000 psi, no greater than about 800 psi, or even no greater than about 600 psi.

Item 50. The fluid transfer assembly of any one of the preceding items, wherein the fluid transfer assembly is adapted to be disposable.

Item 51. The fluid transfer assembly of any one of the preceding items, wherein the fluid transfer assembly is adapted to be a single-use fluid transfer assembly.

Item 52. The method of any one of the preceding items, wherein forming a fluid connector comprises overmolding a fluid connector about the tubes.

Item 53. The method of any one of the preceding items, wherein forming a fluid connector comprises contacting the plurality of tubes with a flowable fluid connector composition and curing the flowable fluid connector composition to form the fluid connector.

Item 54. The method of any one of the preceding items, wherein forming a shell comprises overmolding the shell over the fluid connector such that the fluid connector is essentially encapsulated by the shell.

Item 55. The method of any one of the preceding items, wherein the method further comprises sterilizing the fluid connection.

Item 56. The method of any one of the preceding items, wherein the method further comprises sterilizing the inner cavities of the tubes and fluid connector.

Item 57. The method of any one of the preceding items, wherein the method further comprises sterilizing the fluid connection after formation of the shell.

Item 58. The method of any one of the preceding items, wherein the method further comprises sterilizing the fluid connection before formation of the shell.

Item 59. The method of any one of the preceding items, wherein the method further comprises treating the outer surface of the fluid connector before formation of the shell.

Item 60. The method of any one of the preceding items, wherein the method further comprises treating the outer surface of the fluid connector by increasing the surface roughness.

Item 61. The method of any one of the preceding items, wherein the method further comprises treating the outer surface of the fluid connector by chemically treating.

Item 62. The method of any one of the preceding items, wherein treating the outer surface of the fluid connector is adapted to improve the coupling between the fluid connector and the shell.

Item 63. The method of any one of the preceding items, wherein the method further comprises forming one or more outer surface features on the fluid connector.

Item 64. The method of any one of the preceding items, wherein the one or more outer surface features comprises a protrusion, a depression, a groove, a channel, or combinations thereof.

Item 65. The method of any one of the preceding items, wherein the one or more outer surface features are adapted to improve the coupling between the fluid connector and the shell.

Item 66. The fluid connection, fluid transfer assembly, or method of any one of the preceding items, wherein the fluid connection is essentially free of an adhesive.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A fluid connection comprising:
   a. a plurality of flexible polymeric tubes;
   b. an integral fluid connector coupled to and in fluid communication with each of the plurality of tubes, wherein the fluid connector is covalently bonded to the tubes,
   c. a shell disposed over and encapsulating the fluid connector, wherein the fluid connection has a working pressure of at least about 120 psi, wherein the shell is overmolded over the fluid connector such that the fluid connector is essentially encapsulated by the shell.

2. The fluid connection of claim 1, wherein the polymeric tubes have an aseptic inner cavity, the fluid connector has an aseptic inner cavity, the inner cavity of the polymeric tubes is in fluid communication with the inner cavity of the fluid connector, and the shell is composed of a material which is non-autoclavable.

3. The fluid connection of claim 1, wherein a coupling of the fluid connector with the plurality of tubes is the first point of failure in the working pressure of the fluid connection before addition of the shell, and wherein after addition of the shell disposed over and encapsulating the fluid connector, the coupling of the fluid connector with the plurality of tubes is not the first point of failure in the working pressure of the fluid transfer assembly.

4. The fluid connection of claim 1, wherein at least one of the tubes comprises a biopharmaceutical tube.

5. The fluid connection of claim 1, wherein at least one of the tubes comprises a thermoplastic elastomer.

6. The fluid connection of claim 1, wherein at least one of the tubes comprises a reinforced silicone tube.

7. The fluid connection of claim 1, wherein the fluid connector is integral with the tubes.

8. The fluid connection of claim 1, wherein the fluid connector has a shape of a tee, wye, elbow, cross joint, or straight connector.

9. The fluid connection of claim 1, wherein the outer surface of fluid connector comprises one or more surface features comprising a protrusion, a depression, a groove, a channel, or combinations thereof.

10. The fluid connection of claim 1, wherein the shell comprises a polypropylene.

11. The fluid connection of claim 1, wherein the shell is monolithic.

12. The fluid connection of claim 1, wherein the shell has a hardness greater than the hardness of the fluid connector and the hardness of the tubing.

13. The fluid connection of claim 1, wherein the shell is composed of a material that is incompatible with the tubing and the fluid connector.

14. A fluid transfer assembly comprising one or more of the fluid connections according to claim 1.

15. An autoclavable biopharmaceutical fluid connection comprising:
  a. a plurality of silicone reinforced tubes;
  b. an integral silicone fluid connecter coupled to the plurality of tubes such that there is an essentially seamless transition between the inner cavity of the plurality of tubes and the fluid connector, and wherein the fluid connector is covalently bonded to the tubes; and
  c. a polypropylene shell disposed over and encapsulating fluid connector, wherein the fluid connection has a working pressure of at least about 120 psi.

16. A method of forming a fluid connection, the method comprising:
  a. providing a plurality of tubes;
  b. integrally forming a fluid connector about the plurality of tubes, wherein the fluid connector is covalently bonded to the tubes;
  c. forming a shell over and encapsulating the fluid connector, wherein the fluid connection has a working pressure of at least about 120 psi, wherein forming a shell comprises overmolding the shell over the fluid connector such that the fluid connector is essentially encapsulated by the shell.

17. The method of claim 16, wherein forming a fluid connector comprises overmolding the fluid connector about the tubes.

\* \* \* \* \*